United States Patent
Wolf et al.

(10) Patent No.: US 6,455,080 B1
(45) Date of Patent: Sep. 24, 2002

(54) CHEWING GUM CONTAINING CONTROLLED RELEASE ACYCLIC CARBOXAMIDE AND METHOD OF MAKING

(75) Inventors: Fred R. Wolf, West Des Moines, IA (US); Gordon N. McGrew, Evanston; Henry T. Tyrpin, Palos Park, both of IL (US)

(73) Assignee: WM. Wrigley Jr., Company, Chicago, IL (US)

( * ) Notice: Subject to any disclaimer, the term of this patent is extended or adjusted under 35 U.S.C. 154(b) by 0 days.

(21) Appl. No.: 09/527,169

(22) Filed: Mar. 16, 2000

Related U.S. Application Data

(63) Continuation of application No. PCT/US97/24166, filed on Dec. 29, 1997.

(51) Int. Cl.⁷ ............................. A23G 3/30; A61K 9/68
(52) U.S. Cl. ............................. 426/3; 424/48; 424/440
(58) Field of Search ...................... 426/3, 5, 6; 428/48, 428/440

(56) References Cited

U.S. PATENT DOCUMENTS

| | | | |
|---|---|---|---|
| 3,639,569 A | 2/1972 | Medcalf, Jr. ................. | 424/48 |
| 3,644,613 A | 2/1972 | Moeller et al. ............... | 424/49 |
| 3,720,762 A | 3/1973 | Hatasa et al. ................. | 424/58 |
| 3,793,446 A | 2/1974 | Moeller et al. ............... | 424/48 |
| 4,029,759 A | 6/1977 | Humbert et al. .............. | 424/49 |
| 4,033,994 A | 7/1977 | Watson et al. ................ | 426/538 |
| 4,034,109 A | 7/1977 | Rowsell et al. ............... | 424/311 |
| 4,060,091 A | 11/1977 | Watson et al. ................ | 131/9 |
| 4,070,449 A | 1/1978 | Rowsell et al. ............... | 424/45 |
| 4,081,480 A | 3/1978 | Evers et al. .................. | 252/522 |
| 4,105,801 A | 8/1978 | Dogliotti ..................... | 426/99 |
| 4,127,677 A | 11/1978 | Fronczkowski et al. ....... | 426/5 |
| 4,136,163 A | 1/1979 | Watson et al. ................ | 424/154 |
| 4,139,639 A | 2/1979 | Bahoshy et al. .............. | 426/3 |
| 4,146,653 A | 3/1979 | Mader et al. ................. | 427/3 |
| 4,153,679 A | 5/1979 | Rowsell et al. ............... | 424/45 |
| 4,157,384 A | 6/1979 | Watson et al. ................ | 424/45 |
| 4,190,643 A | 2/1980 | Watson et al. ................ | 424/54 |
| 4,230,687 A | 10/1980 | Sair et al. .................... | 424/22 |
| 4,230,688 A | 10/1980 | Rowsell et al. ............... | 424/45 |
| 4,248,859 A | 2/1981 | Rowsell et al. ............... | 424/54 |
| 4,296,093 A | 10/1981 | Rowsell et al. ............... | 424/45 |
| 4,296,255 A | 10/1981 | Rowsell et al. ............... | 564/515 |
| 4,317,838 A | 3/1982 | Cherukuri et al. ............ | 426/5 |
| 4,318,900 A | 3/1982 | Rowsell et al. ............... | 424/54 |
| 4,384,004 A | 5/1983 | Cea et al. ..................... | 426/3 |
| 4,386,106 A | 5/1983 | Merrit et al. .................. | 426/5 |
| 4,423,086 A | 12/1983 | Devos et al. .................. | 427/3 |
| 4,459,425 A | 7/1984 | Amano et al. ................ | 568/666 |
| 4,515,769 A | 5/1985 | Merritt et al. ................. | 424/49 |
| 4,597,970 A | 7/1986 | Sharma et al. ................ | 426/5 |
| 4,634,593 A | 1/1987 | Stroz et al. ................... | 426/5 |
| 4,671,967 A | 6/1987 | Patel et al. ................... | 426/658 |
| 4,681,766 A | 7/1987 | Huzinec et al. ............... | 426/5 |
| 4,724,151 A | 2/1988 | Mansukhani et al. .......... | 426/3 |
| 4,753,790 A | 6/1988 | Silva et al. ................... | 424/440 |
| 4,786,511 A | 11/1988 | Huzinec et al. ............... | 426/5 |
| 4,792,453 A | 12/1988 | Reed et al. .................... | 426/5 |
| 4,828,845 A | 5/1989 | Zamudio-Tena et al. ....... | 426/5 |
| 4,840,797 A | 6/1989 | Boursier ...................... | 424/475 |

(List continued on next page.)

FOREIGN PATENT DOCUMENTS

| | | |
|---|---|---|
| CA | 2101790 | 2/1994 |
| DE | 24 33 165 | 1/1975 |
| DE | 26 08 226 | 9/1977 |
| FR | 2577922 | 2/1986 |
| GB | 1315625 | 5/1973 |
| GB | 1404596 | 9/1975 |
| GB | 1411785 | 10/1975 |
| GB | 1411786 | 10/1975 |
| GB | 1421743 | 1/1976 |
| GB | 1421744 | 1/1976 |
| GB | 1422998 | 1/1976 |
| GB | 1476351 | 6/1977 |
| GB | 1502680 | 3/1978 |
| GB | 2115672 | 9/1983 |
| JP | 94-065023 | 3/1984 |
| WO | WO 84/03201 | 8/1984 |
| WO | Wo 89/05590 | 6/1989 |
| WO | WO 90/11020 | 10/1990 |
| WO | WO 90/14015 | 11/1990 |
| WO | WO 91/03147 | 3/1991 |
| WO | WO 94/06308 | 3/1994 |
| WO | WO 94/10117 | 5/1994 |
| WO | WO 95/07622 | 3/1995 |
| WO | WO 95/07625 | 3/1995 |
| WO | WO 95/08925 | 4/1995 |
| WO | WO 96/17524 | 6/1996 |
| WO | WO 96/28133 | 9/1996 |
| WO | WO 97/07771 | 3/1997 |
| WO | WO 97/24036 | 7/1997 |

OTHER PUBLICATIONS

Voirol, F. "Chewing Gum History: Xylitol Sweetened Chewing Gum" subtitle "The Evolution of Chewing Gum: Xylitoy and the Prevention of Dental Caries", published Mar., 1985, pp 1–76.

*Primary Examiner*—Arthur L. Corbin
(74) *Attorney, Agent, or Firm*—Steven P. Schurtz; Brinks Hofer Gilson & Lione

(57) ABSTRACT

A method for producing a chewing gum, as well as the chewing gum so produced, includes incorporating a modified release acyclic carboxamide into the gum composition. In one embodiment an acyclic carboxamide is made in a modified release structure and formed into particles. The modified release acyclic carboxamide is preferably obtained by physically modifying the properties of the acyclic carboxamide by coating and drying. When incorporated into gum, these particles are adapted to enhance the shelf stability of the flavor and/or produce a modified release when the gum is chewed.

23 Claims, No Drawings

U.S. PATENT DOCUMENTS

| | | | |
|---|---|---|---|
| 4,961,935 A | 10/1990 | Cherukuri et al. | 426/3 |
| 4,978,537 A | 12/1990 | Song | 426/5 |
| 5,009,893 A | 4/1991 | Cherukuri et al | 424/440 |
| 5,128,155 A | 7/1992 | Song et al. | 426/5 |
| 5,165,943 A | 11/1992 | Patel et al. | 426/3 |
| 5,248,508 A | 9/1993 | Reed et al. | 426/5 |
| 5,266,592 A | 11/1993 | Grub et al. | 514/452 |
| 5,270,061 A | 12/1993 | Reed et al. | 426/5 |
| 5,326,574 A | 7/1994 | Chapdelaine et al. | 426/5 |
| 5,348,750 A | 9/1994 | Greenberg | 426/3 |
| 5,372,824 A | 12/1994 | Record et al. | 426/3 |
| 5,376,389 A | 12/1994 | Reed et al. | 426/5 |
| 5,409,715 A | 4/1995 | Meyers | 426/5 |
| 5,451,404 A | 9/1995 | Furman | 424/401 |
| 5,478,593 A | 12/1995 | Serpellioni et al. | 426/303 |
| 5,527,542 A | 6/1996 | Serpellioni et al. | 424/488 |
| 5,536,511 A | 7/1996 | Yatka | 426/5 |
| 5,571,547 A | 11/1996 | Serpellioni et al. | 426/103 |
| 5,578,339 A | 11/1996 | Kunz et al. | 426/658 |
| 5,603,970 A | 2/1997 | Tyrpin et al. | 426/5 |
| 5,665,406 A | 9/1997 | Reed et al. | 426/5 |
| 5,716,652 A | 2/1998 | Barkalow et al. | 426/5 |
| 5,725,865 A | 3/1998 | Mane et al. | |
| 5,827,852 A | 10/1998 | Russell et al. | |
| 5,843,466 A | 12/1998 | Mane et al. | |
| 6,231,900 B1 | 5/2001 | Hanke | |

CHEWING GUM CONTAINING CONTROLLED RELEASE ACYCLIC CARBOXAMIDE AND METHOD OF MAKING

CROSS REFERENCE TO RELATED APPLICATION

The present application is a continuation of Application Serial No. PCT/US97/24166, filed Dec. 29, 1997, designating the United States, which claims the benefit under 35 U.S.C. § 119(a)-(d) of application Serial No. PCT/US97/16731, filed Sep. 18, 1997, designating the United Kingdom. Both of the foregoing applications are hereby incorporated by reference.

BACKGROUND OF THE INVENTION

The present invention relates to chewing gum compositions and methods of producing chewing gum. More particularly, the invention relates to producing chewing gum containing a physiological cooling agent, specifically acyclic carboxamide. Preferably the physiological cooling agent has been treated to control its release and enhance shelf life stability.

In recent years, efforts have been devoted to controlling release characteristics of various ingredients in chewing gum. Efforts have been directed at perfecting the use of high-intensity sweeteners within the chewing gum formulation, to thereby increase the shelf-life stability of the ingredients, i.e., the protection against degradation of the high-potency sweetener over time.

Patent Cooperation Treaty Publication No. WO 89/03170 discloses a method of controlling the release of acesulfame K. In this process, the sweetener is encapsulated fully or partially to modify the release rate in chewing gum.

Other patent publications disclose how a sweetener like aspartame can be physically modified to control its release rate in chewing gum.

For example, U.S. Pat. No. 4,597,970 to Sharma et al. teaches a process for producing an agglomerated sweetener wherein the sweetener is dispersed in a hydrophobic matrix consisting essentially of lecithin, a glyceride and a fatty acid or wax having a melting point between 25 and 100° C. The disclosed method uses a spray congealing step to form the sweetener-containing matrix into droplets, followed by a fluid-bed second coating on the agglomerated particles.

U.S. Pat. Nos. 4,515,769 and 4,386,106, both to Merrit et al., teach a two step process for preparing a delayed release flavorant for chewing gum. In this process, the flavorant is prepared in an emulsion with a hydrophilic matrix. The emulsion is dried and ground and the particles are then coated with a water-impermeable substance.

U.S. Pat. No. 4,230,687 to Sair et al. teaches a process for encasing an active ingredient to achieve gradual release of the ingredient in a product such as chewing gum. The described method involves adding the ingredient to an encapsulating material in the form of a viscous paste. High shear mixing is used to achieve a homogeneous dispersion of the ingredient within the matrix, which is subsequently dried and ground.

U.S. Pat. No. 4,139,639 to Bahoshy et al. teaches a process of "fixing" aspartame by co-drying (by spray drying or fluid bed coating) a solution containing aspartame and an encapsulating agent, such as gum arabic, to thereby surround and protect the aspartame in the gum during storage.

U.S. Pat. No. 4,384,004 to Cea et al. teaches a method of encapsulating aspartame with various solutions of encapsulating agents using various encapsulation techniques, such as spray drying, in order to increase the shelf stability of the aspartame.

U.S. Pat. No. 4,634,593 to Stroz et al. teaches a method for producing controlled release sweeteners for confections, such as chewing gum. The method taught therein involves the use of an insoluble fat material which is mix mulled with the sweetener.

Several known compounds have what can be characterized as a "cooling" activity, and are referred to in the art as "physiological cooling agents." Physiological cooling agents are perceived as cold or cool when contacted with the human body and, in particular, with the mucous membranes of the mouth, nose and throat.

Efforts have been directed at perfecting the use of physiological cooling agents within chewing gum formulations to enhance flavor composition and control their release to enhance the flavor of chewing gum.

U.S. Pat. No. 5,326,574 discloses a process for codrying the physiological cooling agent 3-l-menthoxypropane-1,2-diol with a food acceptable, water-soluble carrier and mixing the resulting product into chewing gum.

Peppermint oil is currently used to create a "cooling" in oral products such as toothpaste, mouthwash, chewing gum, candy and other food products. Peppermint oil generally comprises about 45% menthol, about 20% menthone, about 5% menthyl acetate, about 5% eucalyptol and many other constituents. Peppermint oil is even used in non-peppermint products, such as spearmint or wintergreen flavored products, in order to create this desired cooling effect. However, peppermint notes are then found in the resulting non-peppermint flavored products.

Menthol is also known for its physiological cooling effect on the skin and mucous membranes of the mouth. Being a major constituent of peppermint oil, menthol has been used extensively in foods, beverages, dentrifices, mouthwashes, toiletries, lotions and the like. The disadvantages of using menthol, however, are its strong minty odor and the harsh notes it imparts to compositions in which it is found.

A need, therefore, exists for a cooling flavor composition that will contribute a long-lasting cooling sensation to products in which it is found without the unwanted harshness or flavor characteristics that come from adding menthol.

It would be desirable to provide a high flavor impact chewing gum that does not manifest the harsh notes normally associated with some chewing gum. It would also be desirable to provide a clean, high-quality flavored chewing gum with an extended cooling effect.

SUMMARY OF THE INVENTION

This invention incorporates a physiological cooling agent, specifically acyclic carboxamide, or combination of physiological cooling agents with acyclic carboxamide, into a chewing gum. One preferred embodiment contains a flavor, and a combination of physiological cooling agents which have been treated so as to modify their release from the chewing gum. The result is a synergy between the physiological cooling agents and the flavor, which provides a high flavor impact at a lower concentration of flavor. Thus, with the aspects of the present invention, chewing gum can be made with a long lasting cooling sensation without unwanted harshness or flavor characteristics. The gum may have a high flavor impact, as well as a clean, high quality flavor with extended cooling effect.

In a second aspect, the present invention also includes a method for producing chewing gum with an acyclic carboxamide physiological cooling agent or combinations of physiological cooling agents with an acyclic carboxamide, treated to have a modified-release. The controlled release of the physiological cooling agent is obtained by modifying the cooling agent by encapsulation, partial encapsulation or partial coating, entrapment or absorption with water-soluble materials or water-insoluble materials. The procedures for modifying the physiological cooling agent include spray drying, spray chilling, fluid-bed coating, coacervation, extrusion, and other agglomerating and standard encapsulating techniques. The cooling agent may also be absorbed onto an inert or water-insoluble material. The cooling agent may be modified in a multiple step process comprising any of the processes noted.

The combination of cooling agents, when modified according to the present invention, give a chewing gum a controlled-release cooling agent. A higher quantity of cooling agents can be used without resulting in a high initial cooling agent impact, but instead having a delayed cooling release in chewing gum, giving a highly consumer-acceptable chewing gum product. Some cooling agents have a very slow release, but may be modified to give a fast release for more initial impact.

DETAILED DESCRIPTION OF THE PRESENTLY PREFERRED EMBODIMENTS OF THE INVENTION

In the context of this invention, chewing gum refers to chewing gum, bubble gum and the like. Moreover, all percentages are based on weight percentages unless otherwise specified. Further, although some terms are referred to in the singular, it is understood that such references may also encompass the plural.

The composition of a chewing gum tends to suppress the release of its flavors. Although a slow flavor release is desirable in many instances, some consumers prefer a burst of intense flavor. One method to provide a chewing gum with a greater flavor impact is the addition of encapsulated flavor to a chewing gum. For example, for a cool and refreshing taste, cooling flavors such as encapsulated menthol and/or mint flavors are added to chewing gum. A menthol/mint combination is disclosed in U.S. Pat. No. 4,724,151.

However, the improved flavor impact of adding cooling flavors to the chewing gum is somewhat offset by the disadvantage of the bitter, harsh, burning sensations associated with high concentrations of such flavors. This disadvantage is particularly acute for sugarless gum, since sugar tends to mask the harsh notes.

The inventors have found that adding a physiological cooling agent, specifically an acyclic carboxamide that has a modified release from the chewing gum, provides a favorable flavor impact. As a result, the inventors are able to reduce or eliminate the harsh notes associated with the prior art high flavor-impact chewing gums, even in the case of sugarless chewing gums.

By adding a acyclic carboxamide to a menthol or mint type flavored chewing gum, one can obtain a strong cooling and clean minty flavor, without the higher concentrations of menthol or mint flavors required in the prior art. Also, the fast release encapsulation of an acyclic carboxamide complements the mint flavors to give a high impact of flavor and cooling normally found in chewing gum. This cooling effect is like menthol cooling, but without the bitterness associated with menthol.

While there are references that disclose the use of acyclic carboxamide in chewing gum and other confections, controlled release is a new area of interest. Because a flavor imparts a distinct and unique sensation when it is used in a chewing gum, acyclic carboxamide offers unique advantages and may be combined with various types of flavors or with various methods of encapsulation and entrapment for controlled release.

Several U.S. and foreign references disclose the acyclic carboxamides that are physiological cooling agents that may be used in the present invention. Some of these disclose the use of physiological cooling agents in chewing gum. These acyclic carboxamides (AC) include those disclosed in U.S. Pat. Nos. 4,296,255; 4,230,688; and 4,153,679; all assigned to Wilkinson Sword, especially N-2,3-trimethyl-2-isopropyl butanamide (called WS-23); and N-ethyl -2,3-dimethyl -2-isopropyl butanamide. WS-23 is available from ChiRex, Inc. of Wellesley, Mass.

The concentration of physiological cooling agent will depend on the intensity of the physiological cooling agent and the desired cooling effect. In general the concentration of cooling agents used is between about 0.001% and about 2% by weight of the chewing gum. The preferred concentration of cooling agent is between about 0.01 % and about 1.0%, more preferably between 0.02% and about 0.5%.

Acyclic carboxamide provide both moderate release and slow release to give flavor impact and flavor extension. Physical modifications of the physiological cooling agents by encapsulation with another substrate will modify their release in chewing gum by modifying the solubility or dissolution rate. Any standard technique which gives partial or full encapsulation of the combination of acyclic carboxamide can be used. These techniques include, but are not limited to, spray drying, spray chilling, fluid-bed coating, and coacervation. These encapsulation techniques that give partial encapsulation or full encapsulation can be used individually or in any combination in a single step process or multiple step process. Generally, a modified release of acyclic carboxamide is obtained in multistep processes like spray drying the acyclic carboxamide and then fluid-bed coating the resultant powder.

The encapsulation techniques here described are standard coating techniques and generally give varying degrees of coating from partial to full coating, depending on the coating composition used in the process. Also, the coating compositions may be susceptible to water permeation to various degrees. Generally, compositions that have high organic solubility, good film forming properties and low water solubility give better delayed release of the acyclic carboxamide. Such compositions include acrylic polymers and copolymers, carboxyvinyl polymer, polyamides, polystyrene, polyvinyl acetate, polyvinyl acetate phthalate, polyvinyl pyrrolidone and waxes. Although all of these materials are possible for encapsulation of acyclic carboxamide, only food grade materials should be considered. Two standard food grade coating materials that are good film formers but not water soluble are shellac and Zein. Others which are more water soluble, but good film formers, are materials like agar, alginates, a wide range of cellulose derivative like ethyl cellulose and hydroxypropylmethyl cellulose, dextrin, gelatin and modified starches. These ingredients, which are generally approved for food use, may give a faster release when used as an encapsulant for the acyclic carboxamide. Other encapsulants like acacia or maltodextrin can also encapsulate the acyclic carboxamide, but give a faster release rate of the acyclic carboxamide.

The amount of coating or encapsulating material on the acyclic carboxamide also controls the length of time for their release from chewing gum. Generally, the higher the level of coating and the lower the amount of active acyclic carboxamide, the slower the release of the acyclic carboxamide during mastication. To obtain the desired cooling agent release to blend with a gum's flavor release, the encapsulant should be a minimum of about 20% of the coated cooling agents. Preferably, the encapsulant should be a minimum of about 30% of the coated cooling agents, and most preferably should be a minimum of about 40% of the coated cooling agents. Depending on the coating material, a higher or lower amount of coating material may be needed to give the desired release of cooling agents.

Another method of giving a delayed release of the acyclic carboxamide is agglomeration with an agglomerating agent which partially coats the cooling agents. This method includes the step of mixing the acyclic carboxamide and agglomerating agent with a small amount of water or solvent. The mixture is prepared in such a way as to have individual wet particles in contact with each other so a partial coating can be applied. After the water or solvent is removed, the mixture is ground and used as a powdered coated cooling agent.

Materials that can be used as the agglomerating agent are the same as those used in the encapsulation mentioned previously. However, since the coating is only a partial encapsulation, some agglomeration agents are more effective in delaying release than others. Some of the better agglomerating agents are the organic polymers like acrylic polymer and copolymers, polyvinyl acetate, polyvinylpyrrolidone, waxes, shellac and Zein. Other agglomerating agents are not as effective in giving a delayed release as are the polymers, waxes, shellac and Zein, but can be used to give some delayed release. These others agglomerating agents include, but are not limited to, agar, alginates, a wide range of cellulose derivatives, dextrin, gelatin, modified starches, and vegetable gums like guar gums, locust bean gum, and carrageenan. Even though the agglomerated cooling agents are only partially coated, when the quantity of coating is increased compared to the quantity of the cooling agents, the release can be delayed for a longer time during mastication. The level of coating used in the agglomerated product is a minimum of about 5%. Preferably the coating level is a minimum of about 15%, and more preferably about 20%. Depending on the agglomerating agent, a higher or lower amount of agent may be needed to give the desired release of cooling agents.

The acyclic carboxamide may be coated in a two-step process or multiple step process. The acyclic carboxamide may be encapsulated with any of the materials as described previously and then the encapsulated material can be agglomerated as described previously to obtain an encapsulated/agglomerated product that could be used in chewing gum to give a delayed release.

In another embodiment of this invention, the acyclic carboxamide may be absorbed onto another component, often referred to as a carrier, which is porous and become entrapped in the matrix of the porous component. Common materials used for absorbing the acyclic carboxamide include, but are not limited to, silicas, silicates, pharmasorb clay, sponge-like beads or microbeads, amorphous carbonates and hydroxides, including aluminum and calcium lakes, vegetable gums and other spray dried materials.

Depending on the type of absorbent material and how it is prepared, the amount of the acyclic carboxamide that can be loaded onto the absorbent will vary. Generally materials like polymers or spongelike beads or microbeads, amorphous sugars, and alditols and amorphous carbonates and hydroxides absorb about 10% to about 40% of the weight of the absorbent. Other materials like silicas and pharmasorb clays may be able to absorb about 20% to about 80% of the weight of the absorbent.

The general procedure for absorbing the acyclic carboxamide onto the absorbent is as follows. An absorbent like fumed silica powder can be mixed in a powder blender and a solution of the acyclic carboxamide can be sprayed onto the powder as mixing continues. The solution can be about 5% to 30% cooling agent, and higher levels may be used if higher temperatures are used. Generally water is the solvent, but other solvents like alcohol should also be used if approved for use in food. As the powder mixes, the liquid is sprayed onto the powder. Spraying is stopped before the mix becomes damp. The still flowing powder is removed from the mixer and dried to remove the water or other solvent, and ground to a specific particle size.

After the acyclic carboxamide is absorbed onto an absorbent or fixed onto an absorbent, the fixative/cooling agents can be coated by encapsulation. Either full or partial encapsulation may be used, depending on the coating composition used in the process. Full encapsulation may be obtained by coating with a polymer as in spray drying, spray chilling, fluid-bed coating, extrusion, coacervation, or any other standard technique. A partial encapsulation or coating can be obtained by agglomeration of the fixative/cooling agents mixture using any of the materials discussed above.

The acyclic carboxamide can be treated to modify its release by being entrapped in an extrusion process. Examples of such extrusion processes are disclosed in U.S. Pat. No. 5,128,155 and PCT Publication No. WO 94/06308.

The four methods to use to obtain a modified release of acyclic carboxamide are (1) encapsulation by spray drying, fluid-bed coating, spray chilling and coacervation to give full or partial encapsulation; (2) agglomeration to give partial encapsulation; (3) fixation or absorption which also gives partial encapsulation; and (4) entrapment by extrusion. These four methods, combined in any usable manner which physically isolates the acyclic carboxamide, modifies its dissolvability or modifies the release of acyclic carboxamide are included in this invention.

The previously described encapsulated, agglomerated or absorbed acyclic carboxamide may readily be incorporated into a chewing gum composition. Generally the acyclic carboxamide may be added to the gum in either the form of a cooling flavor composition or as part of a modified release combination of acyclic carboxamide. However, both of these aspects of the invention may be used in the same gum formula, and the cooling flavor composition itself or its individual components may be treated to have a modified release. The remainder of the chewing gum ingredients are noncritical to the present invention. That is, the cooling flavor composition and/or coated particles of acyclic carboxamide can be incorporated into conventional chewing gum formulations in a conventional manner. Naturally, the preferred chewing gum formulation is a sugarless formulation. However, the acyclic carboxamide may also be used in a sugar chewing gum. The cooling flavor composition and coated acyclic carboxamide may be used in either regular chewing gum or bubble gum.

In general, a chewing gum compositions typically contain a chewable gum base portion which is essentially free of water and is water-insoluble, a water-soluble bulk portion and flavors which are typically water insoluble. The water-soluble portion dissipates with a portion of the flavor over a period of time during chewing. The gum base portion is retained in the mouth throughout the chew.

The insoluble gum base generally comprises elastomers, elastomer solvents, plasticizers, waxes, emulsifiers and inorganic fillers. Plastic polymers, such as polyvinyl acetate, which behave somewhat as plasticizers, are also often included. Other plastic polymers that may be used include polyvinyl laureate, polyvinyl alcohol and polyvinyl pyrrolidone.

Elastomers may include polyisobutylene, butyl rubber, (isobutylene-isoprene copolymer) and styrene butadiene rubber, as well as natural latexes such as chicle. Elastomer solvents are often resins such as terpene resins. Plasticizers, sometimes called softeners, are typically fats and oils, including tallow, hydrogenated and partially hydrogenated vegetable oils, and coca butter. Commonly employed waxes include paraffin, microcrystalline and natural waxes such as beeswax and carnauba. Microcrystalline waxes, especially those with a high degree of crystallinity, may be considered bodying agents or textural modifiers.

According to the preferred embodiment of the present invention, the insoluble gum base constitutes between about 5% to about 95% by weight of the gum. More preferably the insoluble gum base comprises between 10% and 50% by weight of the gum and most preferably about 20% to 35% by weight of the gum.

The gum base typically also includes a filler component. The filler component may be calcium carbonate, magnesium carbonate, talc, dicalcium phosphate or the like. The filler may constitute between about 5% and about 60% by weight of the gum base. Preferably the filler comprises about 5% to 50% by weight of the gum base.

Gum bases typically also contain softeners including glycerol monostearate and glycerol triacetate. Gum bases may also contain optional ingredients such as antioxidants, colors, and emulsifiers. The present invention contemplates employing any commercially acceptable gum base.

The water-soluble portion of the chewing gum may further comprise softeners, sweeteners, flavors, physiological cooling agents and combinations thereof. The sweeteners often fulfill the role of bulking agents in the gum. The bulking agents typically comprise about 5% to about 95% of the gum composition.

Softeners are added to the chewing gum in order to optimize the chewability and mouth feel of the gum. Softeners, also known in the art as plasticizers or plasticizing agents, generally constitute between about 0.5% to about 15% of the chewing gum. Softeners contemplated by the present invention include glycerin, lecithin and combinations thereof. Further, aqueous sweetener solutions such as those containing sorbitol, hydrogenated starch hydrolysate, corn syrup and combinations thereof may be used as softeners and binding agents in gum.

As mentioned above, the cooling flavor compositions or coated acyclic carboxamides of the present invention will most likely be used in sugarless gum formulations. However, formulations containing sugar are also within the scope of the invention. Sugar sweeteners generally include saccharide-containing components commonly known in the chewing gum art which comprise, but are not limited to, sucrose, dextrose, maltose, dextrin, dried invert sugar, fructose, galactose, corn syrup solids and the like, alone or in any combination.

The coated acyclic carboxamide of the present invention can also be used in combination with sugarless sweeteners. Generally sugarless sweeteners include components with sweetening characteristics but which are devoid of the commonly known sugars and comprise, but are not limited to, sugar alcohols such as sorbitol, hydrogenated isomaltulose, mannitol, xylitol, lactitol, erythintol, hydrogenated starch hydrolysate, maltitol and the like alone or in any combination.

Flavors that may be added to gum include any flavor which is of food acceptable quality commonly known in the art such as essential oils, synthetic flavors or mixtures thereof. Such flavors include, but are not limited to, oils derived from plants and fruits such as citrus oils, fruit essences, peppermint oil, spearmint oil, eucalyptus, other mint oils, clove oil, oil of wintergreen, cinnamic aldehyde, anise and the like. Flavors that are very strong, such as menthol flavors, are also contemplated in this invention. Preferred flavors include cooling flavors such as peppermint, eucalyptus, menthol, wintergreen and fruity-mint; non-cooling flavors such as spearmint and cinnamon; and combinations thereof.

Artificial flavor components are also contemplated by the present invention. Those of ordinary skill in the art will recognize that natural and artificial flavors may be combined in any sensorially acceptable blend. All such flavors and blends are contemplated by the present invention.

The flavor may be added to the chewing gum formula in an amount such that it will contain from about 0.1 % to about 10% flavor, preferably from about 0.2% to about 3.0% flavor, and most preferably about 0.5% to about 2% flavor.

Depending on the particular sweetness release profile and shelf-stability needed, coated or uncoated high-intensity sweeteners may be used in the chewing gum. High-intensity sweeteners, preferably aspartame, may be used at levels from about 0.01% to about 3.0%. Encapsulated aspartame is a high intensity sweetener with improved stability and release characteristics, as compared to free aspartame. Free aspartame can also be added, and a combination of some free and encapsulated aspartame is preferred when aspartame is used.

Optional ingredients such as colors, emulsifiers and pharmaceutical agents may also be added as separate components of the chewing gum composition, or added as part of the gum base.

Aqueous syrups, such as corn syrup and hydrogenated corn syrup may be used, particularly if their moisture content is reduced. This can preferably be done by coevaporating the aqueous syrup with a plasticizer, such as glycerin or propylene glycol, to a moisture content of less than 10%. Preferred compositions include hydrogenated starch hydrolysate solids and glycerin. Such syrups and their methods of preparation are discussed in detail in U.S. Pat. No. 4,671,967.

A preferred method of manufacturing chewing gum according to the present invention is by sequentially adding the various chewing gum ingredients to any commercially available mixer known in the art. After the ingredients have been thoroughly mixed, the gum is discharged from the mixer and shaped into the desired form such as by rolling into sheets and cutting into sticks, extruding into chunks, or casting into pellets.

Generally, the ingredients are mixed by first melting the gum base and adding it to the running mixer. the base may also be melted in the mixer itself. Color or emulsifiers may also be added at this time, along with syrup and a portion of the bulking agent. Further portions of the bulking agent may then be added to the mixer. A flavoring agent is typically added with the final portion of the bulking agent. The coated acyclic carboxamide of the present invention are preferably added after the final portion of bulking agent and flavor have been added. The entire mixing procedure typically takes from five to fifteen minutes, but longer mixing times may sometime be required. Those skilled in the art will recognize that many variations of the above described procedures may be followed.

The acyclic carboxamide, preferably N-2, 3-trimethyl-2-isopropyl butanamide, also called WS-23, may be used in a wide variety of sugarless and sugar chewing gum formulations. WS-23 may be encapsulated or entrapped in a wide variety of controlled release techniques as previously discussed. Gum formulations in which these materials may be used are given in tables 1–7. These formulas may also be made with non-encapsulated acyclic carboxamide. Examples of the techniques and resulting controlled release acyclic carboxamide that may be used in these formulations are discussed in the examples following the tables.

TABLE 1

Regular-Tack Sugarless Gum

|  | Example 1 | Example 2 | Example 3 | Example 4 | Example 5 |
|---|---|---|---|---|---|
| Sorbitol | 50.00 | 50.00 | 50.00 | 50.00 | 50.00 |
| Gum Base | 24.70 | 24.70 | 24.70 | 24.70 | 24.70 |
| Lecithin | 0.20 | 0.20 | 0.18 | 0.18 | 0.18 |
| Glycerin | 2.00 | 2.00 | 2.00 | 5.00 | 8.00 |
| Lycasin | 14.40 | 12.00 | 12.00 | 9.00 | 6.00 |
| Mannitol | 7.10 | 9.50 | 9.48 | 9.53 | 9.53 |
| Peppermint Flavor | 1.40 | 1.40 | 1.44 | 1.44 | 1.44 |
| Active Level of Cooling Agents | 0.20 | 0.20 | 0.20 | 0.15 | 0.15 |
| TOTAL | 100.00 | 100.00 | 100.00 | 100.00 | 100.00 |

TABLE 2

Regular-Tack Sugarless Gum

|  | Example 6 | Example 7 | Example 8 | Example 9 | Example 10 |
|---|---|---|---|---|---|
| Sorbitol | 49.35 | 49.35 | 49.35 | 49.35 | 49.35 |
| Gum Base | 25.50 | 25.50 | 25.50 | 25.50 | 25.50 |
| Lecithin | 0.20 | 0.20 | 0.20 | 0.20 | 0.20 |
| Glycerin | 8.50 | 9.50 | 7.50 | 8.60 | 8.50 |
| Liquid Sorbitol | 6.80 | 5.80 | 7.80 | 6.80 | 6.90 |
| Mannitol | 8.00 | 8.00 | 8.00 | 8.00 | 8.00 |
| Active Level of Cooling Agents | 0.20 | 0.20 | 0.20 | 0.10 | 0.10 |
| Peppermint Flavor | 1.45 | 1.45 | 1.45 | 1.45 | 1.45 |
| TOTAL | 100.00 | 100.00 | 100.00 | 100.00 | 100.00 |

TABLE 3

Sugarless Pellet Gums for Coating

|  | Example 11 | Example 12 | Example 13 | Example 14 | Example 15 |
|---|---|---|---|---|---|
| Sorbitol | 51.16 | 43.87 | 45.92 | 43.81 | 46.33 |
| Gum Base | 31.01 | 33.00 | 32.71 | 33.03 | 30.97 |
| Glycerin | 6.14 | 8.00 | 7.50 | 7.98 | 7.82 |
| Aspartame | 0.06 | — | 0.10 | — | 0.08 |

TABLE 3-continued

Sugarless Pellet Gums for Coating

|  | Example 11 | Example 12 | Example 13 | Example 14 | Example 15 |
|---|---|---|---|---|---|
| Active Level of Cooling Agents | 0.42 | 0.23 | 0.35 | 0.25 | 0.34 |
| Calcium Carbonate | 10.01 | 13.00 | 12.16 | 12.93 | 13.04 |
| Peppermint Flavor | — | 1.20 | 0.17 | — | 1.01 |
| Menthol | — | 0.50 | — | — | 0.21 |
| Fruit Flavor | — | — | — | 1.50 | — |
| Lemon Flavor | — | — | — | .50 | — |
| Encapsulated Menthol | — | 0.20 | — | — | 0.20 |
| Spearmint Flavor | 1.20 | — | 1.09 | — | — |
| TOTAL | 100.00 | 100.00 | 100.00 | 100.00 | 100.00 |

TABLE 4

Sugarless Bubble Gums

|  | Example 16 | Example 17 | Example 18 | Example 19 |
|---|---|---|---|---|
| Sorbitol | 56.65 | 56.09 | 50.42 | 48.63 |
| Gum Base | 24.00 | 24.59 | 28.00 | 30.10 |
| Lecithin | 1.00 | 0.91 | 0.89 | 0.86 |
| Fruit Flavor | 1.20 | 1.41 | — | — |
| Grape Flavor | — | — | 1.71 | — |
| Strawberry Flavor | — | — | — | 1.41 |
| Evaporated Lycasin/Glycerin* | — | 6.79 | 9.61 | 10.41 |
| Glycerin | 17.00 | 10.00 | 9.00 | 8.21 |
| Free Aspartame | 0.04 | — | 0.06 | 0.17 |
| Active Level of Cooling Agents | 0.11 | 0.21 | 0.31 | 0.21 |
| TOTAL | 100.00 | 100.00 | 100.00 | 100.00 |

*Contains 25% glycerin, 67.5% Lycasin brand hydrogenated starch hydrolsate solids and 7.5% water.

TABLE 5

Sugar Gums

|  | Example 20 | Example 21 | Example 22 | Example 23 | Example 24 |
|---|---|---|---|---|---|
| Sugar | 58.29 | 59.26 | 62.49 | 59.97 | 56.61 |
| Gum Base | 22.38 | 20.60 | 20.08 | 23.17 | 26.80 |
| Corn Syrup | 17.20 | 18.50 | 15.40 | 14.70 | 13.88 |
| Glycerin | 1.09 | 0.83 | 1.00 | 1.00 | 1.30 |
| Active Level of Cooling Agents | 0.10 | 0.20 | 0.15 | 0.25 | 0.20 |
| Lecithin | 0.05 | 0.03 | 0.02 | — | — |
| Peppermint Flavor | 0.89 | 0.58 | 0.86 | 0.91 | 1.21 |
| TOTAL | 100.00 | 100.00 | 100.00 | 100.00 | 100.00 |

TABLE 6

Sugar Gums

| | Example 25 | Example 26 | Example 27 | Example 28 | Example 29 |
|---|---|---|---|---|---|
| Sugar | 54.30 | 45.30 | 49.30 | 40.30 | 45.30 |
| Gum Base | 19.20 | 19.20 | 19.20 | 19.20 | 19.20 |
| Glycerin | 1.40 | 1.40 | 1.40 | 1.40 | 1.40 |
| Corn Syrup | 19.00 | 23.00 | 19.00 | 19.00 | 23.00 |
| Dextrose | — | 5.00 | — | — | — |
| Lactose | 5.00 | — | — | — | — |
| Fructose | — | 5.00 | — | — | — |
| Invert Sugar | — | — | 10.00 | — | — |
| Maltose | — | — | — | 10.00 | — |
| Palatinose | — | — | — | — | 10.00 |
| Spearmint Flavor | 0.90 | 0.90 | 0.90 | 9.90 | 0.90 |
| Active Level of Cooling Agents | 0.20 | 0.20 | 0.20 | 0.20 | 0.20 |
| TOTAL | 100.00 | 100.00 | 100.00 | 100.00 | 100.00 |

TABLE 7

Sugarless Gums

| | Example 30 | Example 31 | Example 32 | Example 33 | Example 34 | Example 35 | Example 36 | Example 37 |
|---|---|---|---|---|---|---|---|---|
| Gum Base | 25.50 | 25.50 | 25.50 | 25.50 | 25.50 | 25.50 | 25.50 | 25.50 |
| Sorbitol | 53.80 | 46.80 | 41.80 | 41.80 | 41.80 | 41.80 | 36.80 | 37.80 |
| Sorbitol Liquid/Lycasin | 17.00 | 14.00 | 6.00 | — | 5.00 | — | — | 11.00[A] |
| Mannitol | — | 10.00 | 8.00 | 8.00 | 8.00 | 8.00 | 8.00 | 8.00 |
| Maltitol | — | — | — | 5.00 | — | — | 5.00 | — |
| Xylitol | — | — | 15.00 | 10.00 | — | — | 5.00 | 10.00 |
| Lactitol | — | — | — | — | 10.00 | — | — | — |
| Hydrogenated Isomaltulose | — | — | — | — | — | 15.00 | 10.00 | — |
| Glycerin | 2.00 | 2.00 | 2.00 | 8.00 | 8.00 | 8.00 | 8.00 | 6.00 |
| Flavor | 1.50 | 1.50 | 1.50 | 1.50 | 1.50 | 1.50 | 1.50 | 1.50 |
| Active Level of Cooling Agents | 0.20 | 0.20 | 0.20 | 0.20 | 0.20 | 0.20 | 0.20 | 0.20 |
| TOTAL | 100.00 | 100.00 | 100.00 | 100.00 | 100.00 | 100.00 | 100.00 | 100.00 |

[A]Lycasin brand hydrogenated starch hydrolsate syrup; all others use 70% sorbitol liquid.

Encapsulated WS-23 may be made by the Examples 38–71 that follow and added to any of the formulas give in the preceding tables.

Encapsulations with water soluble polymers such as HPMC or maltodextrins will give a fast release of cooling agent. Encapsulations with shellac, Zein or PVAC will give a slow release.

EXAMPLE 38

This example contains a cooling agent composition which has 20% WS-23 extruded with 80% polyvinyl acetate.

EXAMPLE 39

This example contains a cooling agent composition which has WS-23 coated with Zein.

EXAMPLE 40

This example contains a cooling agent composition which has 15% WS-23 agglomerated with 85% hydroxypropylmethyl cellulose.

EXAMPLE 41

This example contains a cooling agent composition which has 25% menthyl succinate and 75% WS-23 coated with Zein.

EXAMPLE 42

This example contains a cooling agent composition which has 50% menthyl succinate and 50% WS-23 coated with hydroxypropylmethyl cellulose.

EXAMPLE 43

This example contains a cooling agent composition which has 75% menthyl succinate and 25% WS-23 absorbed onto silica.

EXAMPLE 44

This example contains a cooling agent composition which has 50% menthyl lactate and 50% WS-23 which is agglomerated with Zein.

EXAMPLE 45

This example contains a cooling agent composition which has 25% menthyl lactate and WS-23 which is agglomerated with hydroxypropylmethyl cellulose.

EXAMPLE 46

This example contains a cooling agent composition which has 75% menthyl lactate and 25% WS-23 coated with shellac.

EXAMPLE 47

This example contains a cooling agent composition which has 50% WS-23 and 50% p-menthane carboxamide (WS-3) coated with Zein.

EXAMPLE 48

This example contains a cooling agent composition which has 25% 3-l-menthoxypropane-1,2-diol and 75% WS-23 extruded with polyvinyl acetate.

EXAMPLE 49

A shellac/silica/active cooling agent powder mixture is obtained by fluid-bed coating WS-23 absorbed on silica with an alcohol/shellac solution at 20% solids.

EXAMPLE 50

A Zein/silica/active cooling agent mixture is obtained by fluid-bed coating WS-23 absorbed on silica with an alcohol/Zein solution at 25% solids.

EXAMPLE 51

An 85% wax, 15% active WS-23 powder mixture is obtained by spray chilling a mixture of molten wax and cooling agent.

EXAMPLE 52

A 70% wax, 30% active WS-23 powder mixture is obtained by spray chilling a mixture of molten wax and cooling agent.

EXAMPLE 53

A 70% Zein, 30% active WS-23 powder mixture is obtained by spray drying an aqueous mixture of cooling agent and Zein dispersed in an aqueous, high-pH (pH= 11.6–12.0) media at 15% solids.

EXAMPLE 54

A 20% Zein, 20% shellac, 60% active WS-23 powder mixture is obtained by spray drying an alcohol/shellac/cooling agent mixture and then fluid-bed coating the spray dried product for a second coating of alcohol and Zein.

Examples 38–54 would all give nearly complete encapsulation and would delay the release of the cooling agents when used in gum formulations in tables 1 through 7. The higher levels of coating would give a longer delayed release of the cooling agents than the lower levels of coating.

Other polymers that are more water soluble and used in coating would have less of an effect of delaying the release of the cooling agents.

EXAMPLE 55

An 80% gelatin, 20% active WS-23 powder mixture is obtained by spray drying a gelatin/WS-23 emulsion.

EXAMPLE 56

A 50% hydroxypropylmethyl cellulose (HPMC), 50% active WS-23 powder mixture is obtained by fluid-bed coating WS-23 with an aqueous solution of HPMC at 10% solids.

EXAMPLE 57

A 60% maltodextrin, 40% active WS-23 powder mixture is obtained by spray drying an aqueous emulsion of WS-23 and maltodextrin at 40% solids.

EXAMPLE 58

A 60% gum arabic, 40% active WS-23 powder mixture is obtained by fluid-bed coating absorbed on silica, then with an aqueous solution of gum arabic at 40% solids.

The coated WS-23 from the above examples 55 and 56 when used in the chewing gum formula in tables 1 through 7, would give a moderately fast release of cooling agents. The products coated with maltodextrin and gum arabic in Examples 57 and 58, when used in the gum formula in tables 1 through 7, would give a fast release of the cooling agents.

Cooling agents could also be used in gum after being agglomerated to give modified release of these cooling agents.

EXAMPLE 59

A 15% hydroxypropylmethyl cellulose (HPMC), 85% active WS-23 powder mixture can be prepared by agglomerating WS-23 and HPMC blended together, with water being added, and the resulting product being dried and ground.

EXAMPLE 60

A 15% gelatin, 85% active WS-23 powder mixture can be made by agglomerating 3-l-menthoxypropane -1,2-diol and p-menthane carboxamide (WS-3) compounds and gelatin blended together, with water being added, and the resulting product being dried and ground.

EXAMPLE 61

A 10% Zein, 90% active WS-23 powder mixture can be made by agglomerating WS-23 with an aqueous solution containing Zein, and drying and grinding the resulting product.

EXAMPLE 62

A 15% shellac, 85% active WS-23 powder mixture can be made by agglomerating WS-23 with an alcohol solution containing 25% shellac, and drying and grinding the resulting product.

Examples of multiple step treatments are here described:

EXAMPLE 63

WS-23 is spray dried with maltodextrin at 30% solids to prepare a powder. This powder is then agglomerated with a hydroxypropylmethyl cellulose (HPMC) in a ratio of 85/15 powder/HPMC, wetted with water and dried. After grinding the resulting powder will contain about 68% active cooling agent, 17% maltodextrin and 15% HPMC.

EXAMPLE 64

WS-23 is agglomerated with HPMC in a ratio of 85/15 cooling agent/HPMC. After drying and grinding, the resulting powder is fluid-bed coated with an alcohol shellac solution at about 25% solids to give a final product containing about 60% active cooling agent, 10% HPMC, and about 30% shellac.

EXAMPLE 65

WS-23 is agglomerated with HPMC in a ratio of 85/15 cooling agent/HPMC. After drying and grinding, the resulting powder is agglomerated with a 15% solids, high-pH, aqueous solution of Zein to give a final product containing about 60% active cooling agent, 10% HPMC, and 30% Zein.

EXAMPLE 66

WS-23 is spray dried with a 25% emulsion of gelatin. The spray dried product is then agglomerated with a 15% solids, high-pH, aqueous solution of Zein. The final product will contain about 50% active cooling agent, 20% gelatin, and 30% Zein.

EXAMPLE 67

WS-23 is agglomerated with molten wax in a ratio of 85/15 cooling agent/wax. When the mixture cools and is ground, it is fluid-bed coated with a 10% Zein solution, giving a final product containing 60% active cooling agent, 10% wax, and 30% Zein.

EXAMPLE 68 AND 69

A solution of maltodextrin was prepared by mixing 812 grams of maltodextrin in 2600 grams of hot water. A Brinkman Homogenizer was then used to mix 500 grams of WS-23 and heated to 90° C. This mixture was then spray dried yielding a product analyzed to contain 31 % active WS-23. Two gum samples were then made with unencapsulated and encapsulated WS-23 using the following formulas:

|  | Comparative Example 68 | Example 69 |
|---|---|---|
| Gum Base | 19.65 | 19.65 |
| Sugar | 54.60 | 54.38 |
| Corn Syrup 39 DE, 45 Bé | 13.30 | 13.30 |
| Dextrose Monohydrate | 9.90 | 9.90 |
| Glycerin | 1.30 | 1.30 |
| Peppermint Flavor | 0.90 | 0.90 |
| Lecithin | 0.25 | 0.25 |
| WS-23 | 0.10 | — |
| Spray Dried WS-23 | — | 0.32 |

Sensory evaluation of the two samples showed a significantly faster release of coolness and WS-23 from Example 69 than Comparative Example 68.

EXAMPLE 70

A blend of 20% WS-23, 20% amorphous silicon dioxide, and 60% medium molecular weight polyvinyl acetate was made by dry blending these powders. The blend was then extruded in a twin screw extruder to form fibers and ground. The extrudate was a clean, white, plastic material that was placed in a freezer to make it brittle before grinding to obtain a powder blend. This blend will have a slow release compared to WS-23 added separately.

EXAMPLE 71

A blend of 8% WS-23, 12% amorphous silicon dioxide, 20% aspartame sweetener, and 60% high molecular weight polyvinyl acetate was made by dry blending these powders. The blend was then extruded in a twin screw extruder to form fibers. The extrudate was a clean, white, brittle material that was then ground to obtain a powder blend. This blend will have a slow release compared to WS-23 added separately.

Many of the examples listed are single step processes. However, more delayed release of the cooling agent may be obtained by combining the various processes of encapsulation, agglomeration, absorption, and entrapment. Any of the above preparations can be further treated in fluid-bed coating, spray chilling or coacervation processes to encapsulate the product, and can be agglomerated with various materials and procedures in a variety of multiple step processes.

It should be appreciated that the methods and compositions of the present invention are capable of being incorporated in the form of a variety of embodiments, only a few of which have been illustrated and described above. The invention may be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed is:

1. A method of producing a chewing gum product containing a physically-modified acyclic carboxamide in order to increase the release rate of the acyclic carboxamide from the chewing gum comprising the steps of:
   a) mixing a quantity of an acyclic carboxamide with a modifying agent wherein the modifying agent increases the release rate of the acyclic carboxamide; and
   b) adding a quantity of the mixture to a chewing gum formulation to provide an acyclic carboxamide level in the chewing gum formulation of from about 0.001% to about 2.0%.

2. The method of claim 1 wherein said modifying agent is an encapsulating agent.

3. The method of claim 2 wherein the acyclic carboxamide and encapsulating agent are also mixed with a solvent and the resulting mixture is dried prior to being added to the chewing gum.

4. The method of claim 3 wherein the encapsulating agent is selected from the group consisting of maltodextrin and gum arabic.

5. The method of claim 3 wherein said resulting mixture is spray dried and the solvent comprises water.

6. The method of claim 2 wherein the acyclic carboxamide is fluid-bed coated with a solution of encapsulating agent and solvent in order to increase the rate of release of the acyclic carboxamide from the chewing gum.

7. The method of claim 6 wherein the solvent comprises water.

8. The method of claim 6 wherein a high-potency sweetener selected from the group consisting of aspartame, alitame, salts of acesulfame, cyclamate and its salts, saccharin and its salts, thaumatin, monellin, dihydrochalcones and combinations thereof is mixed in combination with the acyclic carboxamide and the encapsulating agent.

9. The method of claim 6 wherein the acyclic carboxamide comprises N-2,3-trimethyl-2-isopropyl butanamide.

10. The method of claim 9 wherein the encapsulating agent is selected from the group consisting of hydroxypropylmethyl cellulose, dextrin, gelatin, modified starch, acacia and maltodextrin.

11. The method of claim 6 wherein the encapsulating agent is selected from the group consisting of hydroxypropylmethyl cellulose, dextrin, gelatin, modified starch, acacia and maltodextrin.

12. The method of claim 2 wherein the encapsulating agent is selected from the group consisting of hydroxypropylmethyl cellulose, dextrin, gelatin, modified starch, acacia and maltodextrin.

13. The method of claim 1 wherein a high-potency sweetener selected from the group consisting of aspartame, alitame, salts of acesulfame, cyclamate and its salts, saccharin and its salts, thaumatin, monellin, dihydrochalcones and combinations thereof is mixed in combination with the acyclic carboxamide and modifying agent.

14. The method of claim 1 wherein the acyclic carboxamide comprises N-2,3-trimethyl-2-isopropyl butanamide.

15. The method of claim 14 wherein the modifying agent is selected from the group consisting of hydroxypropylmethyl cellulose, dextrin, gelatin, modified starch, acacia and maltodextrin.

16. The method of claim 1 wherein the modifying agent is selected from the group consisting of hydroxypropylmethyl cellulose, dextrin, gelatin, modified starches, acacia and maltodextrin.

17. A chewing gum product made according to the method of claim 1.

18. A method of producing a chewing gum containing physically-modified acyclic carboxamide in order to increase the release rate of the acyclic carboxamide from the chewing gum comprising the steps of:

a) mixing a quantity of the acyclic carboxamide with an agglomerating agent and a solvent to partially coat the acyclic carboxamide;

b) removing the solvent from the mixture of acyclic carboxamide and agglomerating agent to form a dried material; and c) adding a quantity of the dried material to a chewing gum formulation to provide an acyclic carboxamide level in gum of from about 0.001% to about 2%;

d) wherein the agglomerating agent increases the rate of release of the acyclic carboxamide from the chewing gum.

19. The method of claim 18 wherein the level of coating on the agglomerated acyclic carboxamide is at least about 5%.

20. The method of claim 18 wherein the level of coating on the agglomerated acyclic carboxamide is at least about 15%.

21. The method of claim 18 wherein the level of coating on the agglomerated acyclic carboxamide is at least about 20%.

22. The method of claim 18 wherein the dried material is ground to a powder prior to adding the dried material to the chewing gum.

23. The method of claim 18 wherein the agglomerating agent is selected from the group consisting of hydroxypropylmethyl cellulose, dextrin, gelatin, modified starch, acacia and maltodextrin.

* * * * *